(12) United States Patent
Kuroita et al.

(10) Patent No.: US 7,875,637 B2
(45) Date of Patent: *Jan. 25, 2011

(54) BENZIMIDAZOLE DERIVATIVE AND USE AS A II RECEPTOR ANTAGONIST

(75) Inventors: Takanobu Kuroita, Katano (JP); Hiroki Sakamoto, Amagasaki (JP); Mami Ojima, Amagasaki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/458,092

(22) Filed: Jun. 30, 2009

(65) Prior Publication Data

US 2009/0270464 A1 Oct. 29, 2009

Related U.S. Application Data

(63) Continuation of application No. 11/466,633, filed on Aug. 23, 2006, which is a continuation of application No. PCT/JP2005/003422, filed on Feb. 23, 2005, now Pat. No. 7,572,920, and a continuation of application No. 11/031,057, filed on Jan. 7, 2005, now Pat. No. 7,157,584.

(30) Foreign Application Priority Data

Feb. 25, 2004 (JP) ............................. 2004-048928

(51) Int. Cl.
C07D 271/07 (2006.01)
A61K 31/4245 (2006.01)
(52) U.S. Cl. ........................................ 514/364; 548/132
(58) Field of Classification Search ................. 548/132; 514/364
See application file for complete search history.

(56) References Cited

U.S. PATENT DOCUMENTS

| | | | |
|---|---|---|---|
| 5,196,444 | A | 3/1993 | Naka et al. |
| 5,243,054 | A | 9/1993 | Naka et al. |
| 5,310,929 | A | 5/1994 | Ardecky et al. |
| 5,354,766 | A | 10/1994 | Naka et al. |
| 5,583,141 | A | 12/1996 | Naka et al. |
| 5,605,919 | A | 2/1997 | Matsumori |
| 5,610,314 | A | 3/1997 | Cheng et al. |
| 5,616,599 | A | 4/1997 | Yanagisawa et al. |
| 5,646,171 | A | 7/1997 | Yanagisawa et al. |
| 5,736,555 | A | 4/1998 | Naka et al. |
| 5,883,111 | A | 3/1999 | Naka et al. |
| 6,100,252 | A | 8/2000 | Naka et al. |
| 7,157,584 | B2 | 1/2007 | Kuroita et al. |
| 2005/0032854 | A1 | 2/2005 | Kawahara et al. |

FOREIGN PATENT DOCUMENTS

| | | |
|---|---|---|
| EP | 0 520 423 A1 | 12/1992 |
| EP | 1 452 176 | 9/2004 |
| JP | 4-364171 | 12/1992 |
| JP | 5-078328 | 3/1993 |
| JP | 5-271228 | 10/1993 |
| WO | WO 03/047573 | 12/2003 |

OTHER PUBLICATIONS

Farina et al. (Euro. J. of Pharmacology, (1996), v. 310, p. 185-191).*
http://progressreport.cancer.gov/doc.asp?pid=1&did=2005&mid=vcol&chid=21, Circulatory Problems (Peripheral Vascular Disease) accessed Oct. 22, 2007, Oct. 2002 4 pages.
Kaplan, "Angiotensin II Receptor Antagonists in the Treatment of Hypertension," American Family Physician, 1999, 60(4):8 pages.
Kubo et al., "Nonpeptide Angiotensin II Receptor Antagonists. Synthesis and Biological Activity of Potential Prodrugs of Benzimidazole-7-carboxylic Acids," J. Med. Chem., 1993, 36:2343-2349.
Kubo et al., "Nonpeptide Antiogensin II Receptor Antagonists. Synthesis and Biological Activity of Benzimidazoles," J. Med. Chem., 1993, 36(12):1772-1784.
Ura et al., "The mechanisms of insulin sensitivity improving effects of angiotensin converting enzyme inhibitor," Immunopharmacology, 1999, 44:153-159.
Wexler et al., "Nonpeptide Antiogensin II Receptor Antagonists: The Next Generation in Antihypertensive Therapy," J. Med. Chem., 1996, 39(3):625-656.

* cited by examiner

*Primary Examiner*—Robert Havlin
(74) *Attorney, Agent, or Firm*—Foley & Lardner LLP

(57) ABSTRACT

The present invention relates to a compound represented by the formula (I)

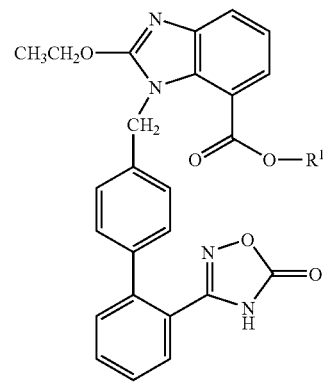

wherein $R^1$ is a group represented by the formula

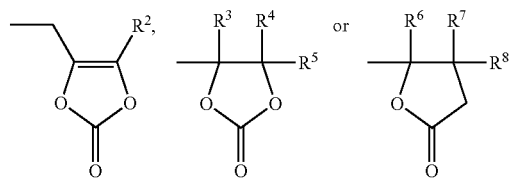

wherein $R^2$, $R^3$, $R^4$, $R^5$, $R^6$, $R^7$ and $R^8$ are each independently a hydrogen atom or a $C_{1-6}$ alkyl, or a salt thereof. The compound of the present invention is useful as an agent for the prophylaxis or treatment of circulatory diseases such as hypertension and the like and metabolic diseases such as diabetes and the like.

5 Claims, No Drawings

BENZIMIDAZOLE DERIVATIVE AND USE AS A II RECEPTOR ANTAGONIST

RELATED APPLICATIONS

This application is a Continuation of U.S. patent application Ser. No. 11/466,633, filed Aug. 23, 2006 now U.S. Pat. No. 7,572,920, which is a Continuation of International Patent Application PCT/JP2005/003422, filed Feb. 23, 2005, and is a Continuation of U.S. patent application Ser. No. 11/031,057, filed Jan. 7, 2005 now U.S. Pat. No. 7,157,584 which claims priority to Japanese Patent Application 048928/2004, filed Feb. 25, 2004.

TECHNICAL FIELD

The present invention relates to a novel benzimidazole derivative having superior properties of a pharmaceutical agent. More particularly, the present invention relates to a prodrug of a benzimidazole derivative having a particular structure, which has a strong and long lasting angiotensin II antagonistic activity and hypotensive action, and an insulin sensitizing activity, and which is useful as an agent for the prophylaxis or treatment of circulatory diseases such as hypertension, cardiac diseases (cardiac hypertrophy, cardiac failure, cardiac infarction and the like), nephritis, stroke and the like and metabolic diseases such as diabetes and the like, and use thereof.

BACKGROUND ART

Angiotensin II causes vasoconstriction via an angiotensin II receptor on the cell membrane and elevates blood pressure. Therefore, an angiotensin II receptor antagonist can be an effective therapeutic drug for circulatory diseases such as hypertension and the like.

As a preferable chemical structure to express strong angiotensin II antagonistic activity, a structure having an acidic group such as a tetrazolyl group, a carboxyl group and the like on a biphenyl side chain is known, and, as a pharmaceutical compound having such structural characteristics, losartan, candesartan cilexetil, olmesartan medoxomil and the like have been clinically used (Ruth R. Wexler et al., Journal of Medicinal Chemistry, vol. 39, p. 625 (1996), JP-A-4-364171, JP-A-5-78328 and the like). JP-A-5-271228 describes that a compound wherein an acidic group on a biphenyl side chain is 5-oxo-4,5-dihydro-1,2,4-oxadiazol-3-yl group exhibits a long lasting and strong angiotensin II antagonistic activity and hypotensive action by oral administration. In addition, WO03/047573 describes that, of the benzimidazole derivatives described in JP-A-5-271228, a particular compound (2-ethoxy-1-{[2'-(5-oxo-4,5-dihydro-1,2,4-oxadiazol-3-yl)biphenyl-4-yl]methyl}-1H-benzimidazole-7-carboxylic acid: compound A) has an insulin sensitizing activity in addition to an angiotensin II antagonistic activity.

As one of the means for enhancing practical use of a pharmaceutical agent, conversion of a compound having a certain pharmacological activity to a prodrug is known. For example, as a prodrug of carboxylic acid, alkylcarbonyloxymethyl ester, 1-alkylcarbonyloxyethyl ester, alkyloxycarbonyloxymethyl ester, 1-alkyloxycarbonyloxyethyl ester and (5-methyl-2-oxo-1,3-dioxol-4-yl)methyl ester have been widely used for a compound that shows insufficient expression of activity by oral administration in the development of pharmaceutical products to the present. In addition, Farnesol ester, which is a liposoluble substance of indomethacin, and ethyl ester as an ACE inhibitor are known to afford sustained activity and the like.

As esters of compound A, methyl ester (compound B), 1-(cyclohexyloxycarbonyloxy)ethyl ester (compound C) and acetoxymethyl ester (compound D) are specifically described in JP-A-5-271228.

The present invention aims at providing a novel compound superior as an agent for the prophylaxis or treatment of circulatory diseases such as hypertension and the like and metabolic diseases such as diabetes and the like.

DISCLOSURE OF THE INVENTION

The present inventors have conducted intensive studies to find a new compound which is more potent and superior in the duration of action by oral administration, thereby to provide a pharmaceutical agent clinically more useful as an agent for the prophylaxis or treatment of circulatory diseases such as hypertension and the like and metabolic diseases such as diabetes and the like.

As a result, they have found that a prodrug compound having a particular structure, which is converted to compound A in the living body, is superior in safety and has extremely superior properties as a pharmaceutical agent, as evidenced by an unexpectedly strong and long lasting hypotensive action, possible stable control of blood pressure for a long time and the like, and completed the present invention.

Accordingly, the present invention relates to (1) a compound represented by the formula (I)

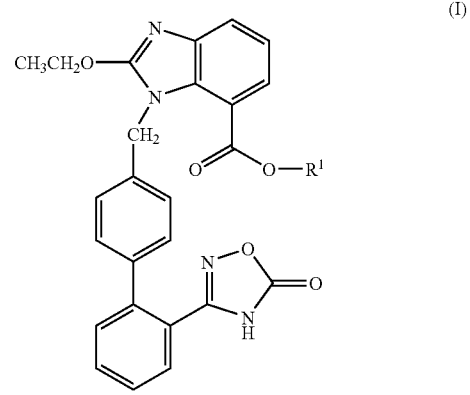

wherein $R^1$ is a group represented by the formula

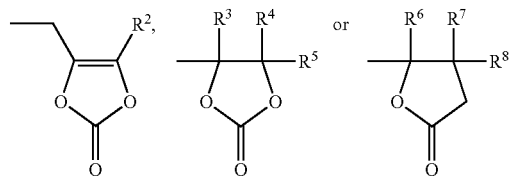

wherein $R^2$, $R^3$, $R^4$, $R^5$, $R^6$, $R^7$ and $R^8$ are each independently a hydrogen atom or a $C_{1-6}$ alkyl, or a salt thereof;

(2) the compound of the aforementioned (1), which is a salt;

(3) the compound of the aforementioned (1), wherein $R^1$ is a group represented by the formula

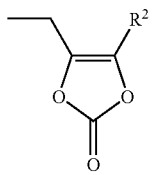

wherein $R^2$ is as defined above;

(4) a compound selected from the group consisting of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate, 2-oxo-1,3-dioxolan-4-yl 2-ethoxy-1-{[2'-(5-oxo-4,5-dihydro-1,2,4-oxadiazol-3-yl)biphenyl-4-yl]methyl}-1H-benzimidazole-7-carboxylate, 4-methyl-2-oxo-1,3-dioxolan-4-yl 2-ethoxy-1-{[2'-(5-oxo-4,5-dihydro-1,2,4-oxadiazol-3-yl)biphenyl-4-yl]methyl}-1H-benzimidazole-7-carboxylate and 5-oxotetrahydro-2-furanyl 2-ethoxy-1-{[2'-(5-oxo-4,5-dihydro-1,2,4-oxadiazol-3-yl)biphenyl-4-yl]methyl}-1H-benzimidazole-7-carboxylate, or a salt thereof;

(5) (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt;

(6) a process for producing a compound represented by the formula

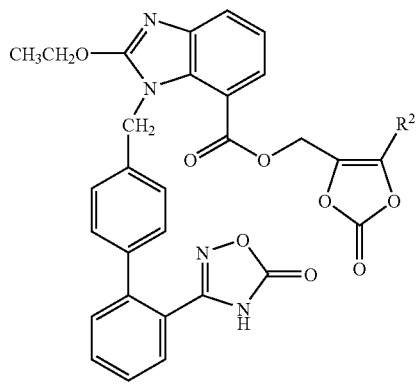

wherein $R^2$ is a hydrogen atom or a $C_{1-6}$ alkyl, or a salt thereof, which comprises reacting a reactive derivative of 2-ethoxy-1-{[2'-(5-oxo-4,5-dihydro-1,2,4-oxadiazol-3-yl)biphenyl-4-yl]methyl}-1H-benzimidazole-7-carboxylic acid or a salt thereof with a compound represented by the formula

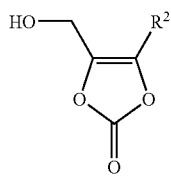

wherein $R^2$ is as defined above, or a salt thereof;

(7) a medicament comprising the compound of the aforementioned (1);

(8) the medicament of the aforementioned (7), which is an angiotensin II antagonist;

(9) the medicament of the aforementioned (7), which is an insulin sensitizer;

(10) the medicament of the aforementioned (7), which is an agent for the prophylaxis or treatment of circulatory diseases;

(11) a medicament comprising the compound of the aforementioned (1) in combination with a calcium antagonist or a diuretic agent;

(12) the medicament of the aforementioned (11), which is an agent for the prophylaxis or treatment of circulatory diseases;

(13) a method for antagonizing angiotensin II in a mammal, which comprises administering an effective amount of the compound of the aforementioned (1) to said mammal;

(14) a method for improving insulin resistance in a mammal, which comprises administering an effective amount of the compound of the aforementioned (1) to said mammal;

(15) a method for preventing or treating of circulatory diseases in a mammal, which comprises administering an effective amount of the compound of the aforementioned (1) to said mammal;

(16) a method for preventing or treating of circulatory diseases in a mammal, which comprises administering an effective amount of the compound of the aforementioned (1) in combination with a calcium antagonist or a diuretic agent to said mammal;

(17) use of the compound of the aforementioned (1) for manufacture of an angiotensin II antagonist;

(18) use of the compound of the aforementioned (1) for manufacture of an insulin sensitizer;

(19) use of the compound of the aforementioned (1) for manufacture of an agent for the prophylaxis or treatment of circulatory diseases;

(20) use of the compound of the aforementioned (1) in combination with a calcium antagonist or a diuretic agent for manufacture of an agent for the prophylaxis or treatment of circulatory diseases; and the like.

DISCLOSURE OF THE INVENTION

In the aforementioned formula, $R^1$ is a group represented by

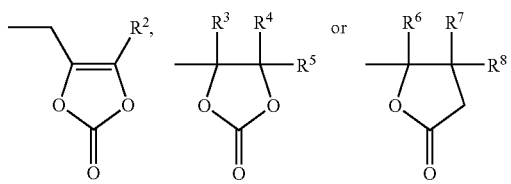

wherein $R^2$, $R^3$, $R^4$, $R^5$, $R^6$, $R^7$ and $R^8$ are each independently a hydrogen atom or a $C_{1-6}$ alkyl, and as the $C_{1-6}$ alkyl, for example, methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, 2-ethylpropyl and the like can be mentioned.

For R[1], a group represented by the formula

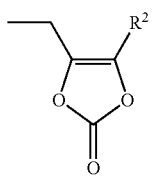

wherein R[2] is as defined above, is preferable and for R[2], methyl is preferable.

In the aforementioned formula, the group represented by the formula

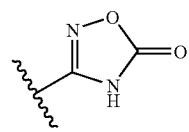

(5-oxo-4,5-dihydro-1,2,4-oxadiazol-3-yl group) includes three tautomers (a•, b• and c•) represented by the formulas

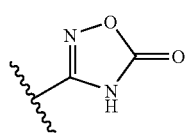    a'

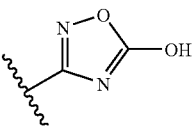    b'

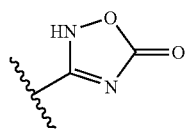    c' and a 5-oxo-4,5-dihydro-1,2,4-oxadiazol-3-yl group encompasses all of the above-mentioned a•, b• and c•.

As a compound represented by the formula (I) of the present invention,
(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate,
2-oxo-1,3-dioxolan-4-yl 2-ethoxy-1-{[2'-(5-oxo-4,5-dihydro-1,2,4-oxadiazol-3-yl)biphenyl-4-yl]methyl}-1H-benzimidazole-7-carboxylate,
4-methyl-2-oxo-1,3-dioxolan-4-yl 2-ethoxy-1-{[2'-(5-oxo-4,5-dihydro-1,2,4-oxadiazol-3-yl)biphenyl-4-yl]methyl}-1H-benzimidazole-7-carboxylate,
5-oxotetrahydro-2-furanyl 2-ethoxy-1-{[2'-(5-oxo-4,5-dihydro-1,2,4-oxadiazol-3-yl)biphenyl-4-yl]methyl}-1H-benzimidazole-7-carboxylate and the like are preferably used. Among them, (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate is particularly preferably used.

The salt of a compound represented by the formula (I) may be any as long as it is a pharmacologically acceptable salt. As such salt, salts of a compound represented by the formula (I) with an inorganic base (e.g., alkali metals such as sodium, potassium and the like; alkaline earth metals such as calcium, magnesium and the like; etc.), an organic base (e.g., organic amines such as tromethamine[tris(hydroxymethyl)methylamine], ethanolamine, trimethylamine, triethylamine, t-butylamine, pyridine, picoline, diethanolamine, triethanolamine, dicyclohexylamine, N,N'-dibenzylethylenediamine and the like; basic amino acids such as arginine, lysine, ornithine and the like; etc.), ammonia and the like, can be mentioned.

As a salt of the compound represented by the formula (I), alkali metal salts of the compound represented by the formula (I) are preferable. Of these, a potassium salt is particularly preferable.

The compound represented by the formula (I) may be labeled with an isotope (e.g., $^3H$, $^{14}C$, $^{35}S$, $^{125}I$ and the like) and the like.

As the compound represented by the formula (I) or a salt thereof (hereinafter sometimes to be referred to as compound (I) or the compound of the present invention), (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt is particularly preferable.

Production Methods

Compound (I) can be produced by, for example, a method shown in the following or a method analogous thereto and the like.

While the yield of compound (I) obtained by the following method may vary depending on the reaction conditions used, compound (I) can be obtained easily at a high purity by a conventional means of separation or purification (e.g., recrystallization, column chromatography and the like) from the product by such methods.

Compound (I) can be produced by reacting a reactive derivative (for example, a mixed acid anhydride, an acid halide and the like) of the compound represented by the formula (II) (compound A) or a salt thereof (hereinafter sometimes to be referred to as compound (II)) with a corresponding alcohol (IV) (HO—R[1]) or a salt thereof.

Method a

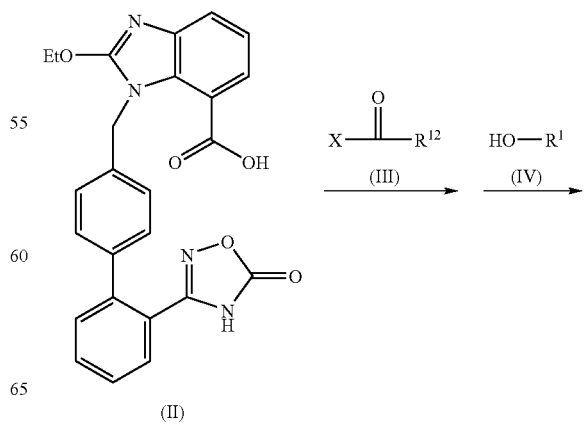

-continued

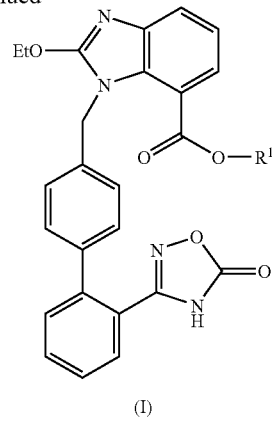

(I)

Method b

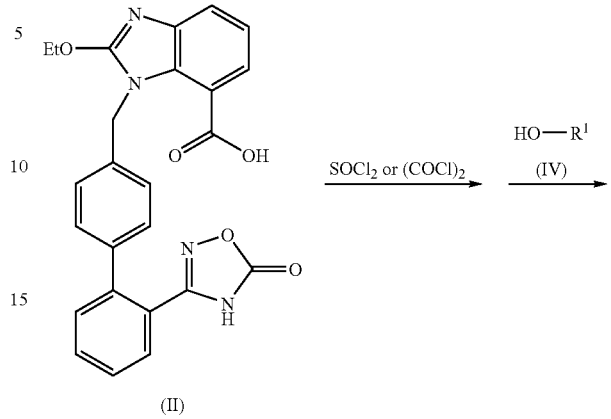

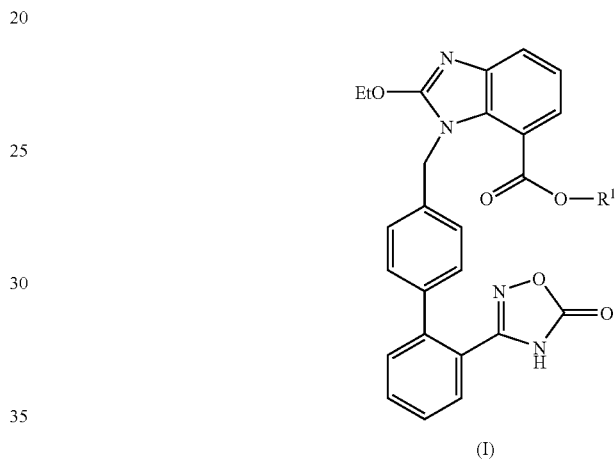

(I)

wherein X is a halogen atom (chlorine, bromine, iodine etc.), Et is an ethyl, $R^{12}$ is an alkyl (e.g., $C_{1-6}$ alkyl such as methyl, ethyl, propyl, t-butyl and the like), an alkoxy (e.g., $C_{1-6}$ alkoxy such as methoxy, ethoxy, isobutyloxy and the like) or a phenyl optionally substituted by halogen atom, $C_{1-6}$ alkyl or nitro group and the like, $R^1$ is as defined above.

Method a comprises reacting compound (II) with an acylating agent (III) in the presence of a base to give a mixed acid anhydride and reacting the resulting compound with a corresponding alcohol (IV) (HO—$R^1$) in the presence of a base to allow esterification.

The mixed acid anhydride is produced using about 1-3 mol of a base and about 1-3 mol of an acylating agent relative to 1 mol of compound (II) in a solvent. Subsequently, the corresponding alcohol is added to allow reaction, or after once filtering off the salt (salt of the base with H—X), concentrating the filtrate, diluting the residue with a solvent and adding the corresponding alcohol and a base to allow reaction to perform esterification.

As the base, triethylamine, diisopropylethylamine, DBU, 4-dimethylaminopyridine, sodium hydride, potassium t-butoxide, potassium carbonate and sodium carbonate and the like can be used.

As the acylating agent, pivaloyl chloride, ethyl chlorocarbonate, isobutyl chlorocarbonate, or 2,4,6-trichlorobenzoyl chloride, 2,6-dichlorobenzoyl chloride, 2,4,6-tribromobenzoyl chloride, 2,3,6-trimethyl-4,5-dinitrobenzoyl chloride and the like described in Bulletin of the Chemical Society of Japan, vol. 52, 1989-1993 page (1979) are used.

As the solvent, generally, dichloromethane, chloroform, 1,2-dichloroethane, ethyl acetate, tetrahydrofuran, toluene, acetonitrile, acetone, ethyl methyl ketone, dioxane, dimethylformamide, dimethylacetamide, dimethyl sulfoxide and the like can be used.

While the reaction conditions for producing a mixed acid anhydride vary depending on the combination of the base, acylating agent and solvent to be used, the reaction is generally preferably carried out at about −30° C. to room temperature for about 1-10 hrs. While the reaction conditions for the esterification vary depending on the combination of the mixed acid anhydride produced and a solvent, the reaction is generally preferably carried out at about −30° C. to the solvent refluxing temperature for about 1-10 hrs.

wherein $R^1$ is as defined above.

Method b comprises reacting a compound represented by the formula (II) or a salt thereof with thionyl chloride or oxalyl chloride in the presence of a catalyst such as DMF and the like to give an acid chloride, and reacting the acid chloride with a corresponding alcohol (IV) in the presence of a base to allow esterification.

The acid chloride is produced using about 1-3 mol of thionyl chloride or oxalyl chloride relative to 1 mol of compound (II) in the presence of a catalytic amount of DMF, in a solvent where necessary. After subsequent concentration, a solvent is added and then the corresponding alcohol (HO—$R^1$) and the base to allow reaction to perform esterification.

As the base, those similar to the bases used in Method a and the like are used.

As the solvent, those similar to the solvents used in Method a and the like are used.

While the reaction conditions for producing an acid chloride vary depending on the solvent to be used, the reaction is generally preferably carried out at about −30° C. to the refluxing temperature for about 10 min. to 5 hrs. The reaction conditions for the esterification vary depending on the combination of the acid chloride produced and the solvent, the reaction is generally preferably carried out at about −30° C. to the refluxing temperature of the solvent for about 1 to 10 hrs.

Method c

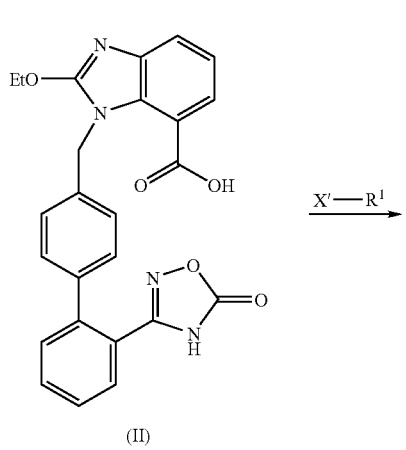

Method d

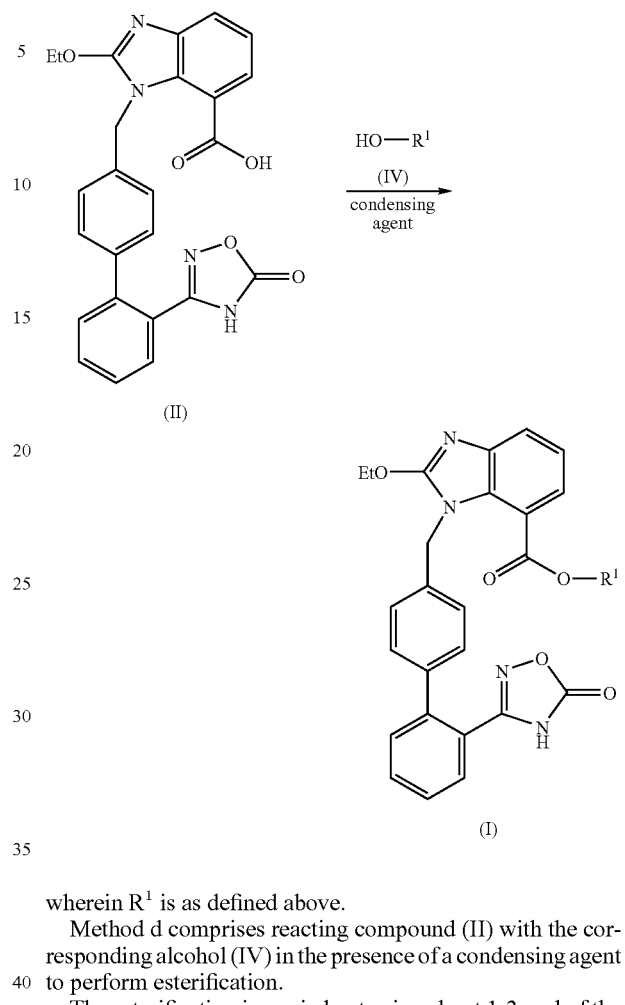

wherein X' is a halogen atom (chlorine, bromine, iodine etc.) and R¹ is as defined above.

Method c comprises reacting a compound represented by the formula (II) or a salt thereof (e.g., salt with alkali metal such as sodium, potassium and the like; salt with alkaline earth metal such as calcium, magnesium and the like; etc.) with an alkylating agent (X'—R¹) as necessary in the presence of a base to allow esterification.

The esterification is carried out using about 1-3 mol of a base and about 1-3 mol of an alkylating agent relative to 1 mol of compound (II) in a solvent.

As the base, those similar to the bases used in Method a and the like are used.

As the solvent, those similar to the solvents used in Method a and the like are used.

While the reaction conditions for the esterification vary depending on the combination of the base, alkylating agent and solvent to be used, the reaction is generally preferably carried out at about −30° C. to the refluxing temperature for about 30 min. to 10 hrs.

wherein R¹ is as defined above.

Method d comprises reacting compound (II) with the corresponding alcohol (IV) in the presence of a condensing agent to perform esterification.

The esterification is carried out using about 1-3 mol of the condensing agent and about 1-3 mol of the corresponding alcohol (IV) relative to 1 mol of compound (II) in a solvent.

As the condensing agent, DCC, WSC, Mitsunobu reagents and the like are used.

As the solvent, those similar to the solvents used in Method a and the like are used.

While the reaction conditions for the esterification vary depending on the combination of the condensing agent and solvent to be used, the reaction is generally preferably carried out at about −30° C. to the refluxing temperature for about 30 min. to 24 hrs.

Compound (II) can be produced by the method described in JP-A-5-271228 and the like.

When compound (I) is obtained as a free form, it can be converted to an object salt by a method known per se or a method analogous thereto. Conversely, when it is obtained as a salt, it can be converted to a free form or a different object salt by a method known per se or a method analogous thereto.

When optical isomers of compound (I) exist, such individual optical isomers and a mixture thereof are all naturally encompassed in the scope of the present invention.

Compound (I) may be a crystal, and may have a form of a single crystal or a form of a mixture of plural crystals. Crystals can be produced by crystallization according to a crystallization method known per se. Compound (I) is preferably a crystal.

Compound (I) may be a solvate (e.g., hydrate etc.) and both solvate and non-solvate (e.g., non-hydrate etc.) are encompassed in the scope of the present invention.

The compound of the present invention thus produced shows lower toxicity and is safe (in other words, more superior as a pharmaceutical agent from the aspects of acute toxicity, chronic toxicity, genetic toxicity, reproductive toxicity, cardiac toxicity, drug interaction, carcinogenicity and the like), and rapidly converted to compound A in the living body of an animal, particularly a mammal (e.g., human, monkey, cat, pig, horse, bovine, mouse, rat, guinea pig, dog, rabbit etc.).

Since compound A normalizes the intracellular insulin signal transduction mechanism, which mainly causes insulin resistance, thereby reducing insulin resistance and enhancing insulin action, and has a glucose tolerance improvement action. Therefore, the compound of the present invention can be used for mammals (e.g., human, monkey, cat, pig, horse, bovine, mouse, rat, guinea pig, dog, rabbit etc.) as an improving agent or an agent for the prophylaxis and/or treatment of the diseases in which insulin resistance is involved. As such diseases, for example, insulin resistance, impaired glucose tolerance; diabetes such as noninsulin dependent diabetes, type II diabetes, type II diabetes associated with insulin resistance, type II diabetes associated with impaired glucose tolerance etc.; various complications such as hyperinsulinemia, hypertension associated with insulin resistance, hypertension associated with impaired glucose tolerance, hypertension associated with diabetes (e.g., type II diabetes etc.), hypertension occurring in association with hyperinsulinemia, insulin resistance occurring in association with hypertension, impaired glucose tolerance occurring in association with hypertension, diabetes occurring in association with hypertension, hyperinsulinemia occurring in association with hypertension, diabetic complications [e.g., microangiopathy, diabetic neuropathy, diabetic nephropathy, diabetic retinopathy, diabetic cataract, large vessel disease, osteopenia, diabetic hyperosmolar coma, infectious diseases (e.g., respiratory infectious disease, urinary tract infectious disease, digestive infectious disease, infectious disease of dermal soft tissue, infectious disease of inferior limb etc.), diabetic gangrene, dry mouth, lowered sense of hearing, diabetic cerebrovascular disorder, diabetic peripheric hematogenous disorder, diabetic hypertension and the like], diabetic cachexia and the like; and the like can be mentioned. The compound of the present invention can also be used for treating patients of high normal blood pressure with diabetes.

Since compound A has a strong angiotensin II antagonistic activity, the compound of the present invention is useful as an agent for the prophylaxis or treatment of a disease (or a disease whose onset is promoted) developed by the contraction or growth of blood vessels or organ disorder, which expresses via an angiotensin II receptor, or due to the presence of angiotensin II, or a factor induced by the presence of angiotensin II, in mammals (e.g., human, monkey, cat, pig, horse, bovine, mouse, rat, guinea pig, dog, rabbit etc.).

As such diseases, for example, hypertension, blood pressure circadian rhythm abnormality, heart diseases (e.g., cardiac hypertrophy, acute heart failure and chronic heart failure including congestive heart failure, cardiac myopathy, angina pectoris, myocarditis, atrial fibrillation, arrhythmia, tachycardia, cardiac infraction etc.), cerebrovascular disorders (e.g., asymptomatic cerebrovascular disorder, transient cerebral ischemia, apoplexy, cerebrovascular dementia, hypertensive encephalopathy, cerebral infarction etc.), cerebral edema, cerebral circulatory disorder, recurrence and sequela of cerebrovascular disorders (e.g., neurotic symptom, psychic symptom, subjective symptom, disorder in daily living activities etc.), ischemic peripheral circulation disorder, myocardial ischemia, venous insufficiency, progression of cardiac insufficiency after cardiac infarction, renal diseases (e.g., nephritis, glomerulonephritis, glomerulosclerosis, renal failure, thrombotic vasculopathy, complication of dialysis, organ dysfunction including nephropathy by radiation damage etc.), arteriosclerosis including atherosclerosis (e.g., aneurysm, coronary arteriosclerosis, cerebral arteriosclerosis, peripheral arteriosclerosis etc.), vascular hypertrophy, vascular hypertrophy or obliteration and organ disorders after intervention (e.g., percutaneous transluminal coronary angioplasty, stenting, coronary angioscopy, intravascular ultrasound, dounce thrombolytic therapy etc.), vascular re-obliteration and restenosis after bypass, polycythemia, hypertension, organ disorder and vascular hypertrophy after transplantation, rejection after transplantation, ocular diseases (e.g., glaucoma, ocular hypertension etc.), thrombosis, multiple organ disorder, endothelial dysfunction, hypertensive tinnitus, other cardiovascular diseases (e.g., deep vein thrombosis, obstructive peripheral circulatory disorder, arteriosclerosis obliterans, obstructive thromboangiitis, ischemic cerebral circulatory disorder, Raynaud's disease, Berger disease etc.), metabolic and/or nutritional disorders (e.g., obesity, hyperlipidemia, hypercholesterolemia, hyperuricacidemia, hyperkalemia, hypernatremia etc.), nerve degeneration diseases (e.g., Alzheimer's disease, Parkinson's syndrome, amyotrophic lateral sclerosis, AIDS encephalopathy etc.), central nervous system disorders (e.g., cerebral hemorrhage, cerebral infarction, their sequela and complication, head injury, spinal injury, cerebral edema, sensory malfunction, sensory functional disorder, autonomic nervous system disorder, autonomic nervous system malfunction, multiple sclerosis etc.), dementia, defects of memory, disorder of consciousness, amnesia, anxiety symptom, catatonic symptom, discomfort mental state, psychopathies (e.g., depression, epilepsy, alcoholism etc.), inflammatory diseases (e.g., arthritis such as rheumatoid arthritis, osteoarthritis, rheumatoid myelitis, periostitis etc.; inflammation after operation and injury; remission of swelling; pharyngitis; cystitis; pneumonia; atopic dermatitis; inflammatory intestinal diseases such as Crohn's disease, ulcerative colitis etc.; meningitis; inflammatory ocular disease; inflammatory pulmonary disease such as pneumonia, pulmonary silicosis, pulmonary sarcoidosis, pulmonary tuberculosis etc.), allergic diseases (e.g., allergic rhinitis, conjunctivitis, gastrointestinal allergy, pollinosis, anaphylaxis etc.), chronic obstructive pulmonary disease, interstitial pneumonia, pneumocytis carinni pneumonia, collagen diseases (e.g., systemic lupus erythematodes, scleroderma, polyarteritis etc.), hepatic diseases (e.g., hepatitis including chronic hepatitis, hepatic cirrhosis etc.), portal hypertension, digestive system disorders (e.g., gastritis, gastric ulcer, gastric cancer, gastric disorder after operation, dyspepsia, esophageal ulcer, pancreatitis, colon polyp, cholelithiasis, hemorrhoidal disease, varices ruptures of esophagus and stomach etc.), blood and/or myelopoietic diseases (e.g., erythrocytosis, vascular purpura, autoimmune hemolytic anemia, disseminated intravascular coagulation syndrome, multiple myelopathy etc.), bone diseases (e.g., fracture, refracture, osteoporosis, osteomalacia, bone Paget's disease, sclerosing myelitis, rheumatoid arthritis, osteoarthritis of the knee and joint tissue dysfunction and the like caused by diseases similar to these etc.), solid tumor, tumors (e.g., malignant melanoma, malignant lymphoma, cancer of digestive organs (e.g., stomach, intestine etc.) etc.), cancer and cachexia following cancer, metastasis cancer, endocrinopathy (e.g., Addison's disease, Cushing's syndrome, pheochromocytoma, primary aldosteronism etc.), Creutzfeldt-Jakob disease, urinary organ and/or male genital diseases (e.g., cystitis, prostatic hypertrophy, prostatic cancer, sex infectious disease etc.), female disorders (e.g., climacteric disorder, gestosis, endometriosis, hysteromyoma, ovarian disease, breast disease, sex infectious disease etc.), disease relating to environment and occupational factors (e.g., radiation hazard, hazard by ultraviolet, infrared or laser beam, altitude sickness etc.), respiratory diseases (e.g., cold syndrome, pneumonia, asthma, pulmonary hypertension, pulmonary thrombosis and pulmonary embolism etc.), infectious diseases (e.g., viral infectious diseases with cytomegalovirus, influenza virus, herpes virus etc., rickettsiosis, bacterial infectious disease etc.), toxemias (e.g., sepsis, septic shock, endotoxin shock, Gram-negative sepsis, toxic shock syndrome etc.), otorhinolaryngological diseases (e.g., Meniere's syndrome, tinnitus, dysgeusia, vertigo, disequilibrium, dysphagia etc.), skin diseases (e.g., keloid, hemangioma, psoriasis etc.), intradialytic hypotension, myasthenia gravis, systemic diseases such as chronic fatigue syndrome and the like can be mentioned.

Since the compound of the present invention can maintain a constant hypotensive action both day and night, reduction of the dose and frequency is possible as compared to the administration of compound A. In addition, it can effectively suppress particularly problematic increase in the blood pressure before and after rising in patients with hypertension.

In addition, by longer term sustained suppression of the action of angiotensin II, the compound of the present invention improves disorder or abnormality or suppresses promotion thereof in the biofunction and physiological action, that causes adult disorders and various diseases linked with aging and the like, which in turn leads to the primary and secondary prophylaxis of diseases or clinical conditions caused thereby or suppression of the progression thereof. As the disorder or abnormality in the biofunction and physiological action, for example, disorder or abnormality in automatic controlling capability of cerebral circulation and/or renal circulation, disorder of circulation (e.g., peripheral, cerebral, microcirculation etc.), disorder of blood-brain-barrier, salt susceptibility, abnormal state of coagulation and fibrinolysis system, abnormal state of blood and blood cell components (e.g., accentuation of platelet aggregation activity, erythrocyte deformability, accentuation of leukocyte adhesiveness, rise of blood viscosity etc.), production and function accentuation of growth factor and cytokines (e.g., PDGF, VEGF, FGF, interleukin, TNF-$\alpha$, MCP-1 etc.), accentuation of proliferation and infiltration of inflammatory cells, accentuation of production of free radical, liposteatosis accentuation, endothelial function disorder, dysfunction of endothelium, cell and organ, edema, cell morphogenesis change of smooth muscle etc. (morphogenesis to proliferation type etc.), production and function accentuation of vasoactive substance and thrombosis inducers (e.g., endothelin, thromboxane $A_2$ etc.), abnormal constriction of blood vessel etc., metabolic disorder (e.g., serum lipid abnormalities, dysglycemia etc.), abnormal growth of cell etc., angiogenesis (including abnormal vasculogenesis during abnormal capillary reticular formation in adventitial coat of arteriosclerosis) and the like can be mentioned. Of these, the present invention can be used as an agent for the primary and secondary prophylaxis or treatment of organ disorders associated with various diseases (e.g., cerebrovascular disorder and organ disorder associated therewith, organ disorder associated with cardiovascular disease, organ disorder associated with diabetes, organ disorder after intervention etc.). In particular, since compound A has an activity of inhibiting proteinuria, the compound of the present invention can be used as an agent for protecting kidney. Therefore, the compound of the present invention can be advantageously used when the patients with insulin resistance, impaired glucose tolerance, diabetes or hyperinsulinemia have concurrently developed the above-mentioned diseases or clinical condition.

Since compound A has an activity of inhibiting body weight gain, the compound of the present invention can be used as a body weight gain inhibitor to mammals. Target mammals may be any mammals of which body weight gain is to be avoided. The mammals may have a risk of body weight gain genetically or may be suffering from lifestyle-related diseases such as diabetes, hypertension and/or hyperlipidemia etc. The body weight gain may be caused by excessive feeding or diet without nutrient balance, or may be derived from combination drug, for example, insulin sensitizers having PPAR$\gamma$-agonistic activity such as troglitazone, rosiglitazone, englitazone, ciglitazone, pioglitazone etc. and the like. In addition, body weight gain may be preliminary to obesity, or may be body weight gain of obesity patients. Here, obesity is defined that BMI (body mass index; body weight (kg)/[height (m)]$^2$) is at least twenty-five for Japanese (criterion by Japan Society for the Study of Obesity), or at least thirty for westerner (criterion by WHO).

The new criteria were reported about diabetic criteria in 1999 by the Japan Diabetes Society.

According to this report, diabetes is a condition wherein the fasting blood glucose level (glucose concentration of venous plasma) is not less than 126 mg/dl, the 2-hour value (glucose concentration of venous plasma) of the 75 g oral glucose tolerance test (75 g OGTT) is not less than 200 mg/dl, or the casual blood glucose level (glucose concentration of venous plasma) is not less than 200 mg/dl. In addition, a condition which does not fall under the above-mentioned diabetes, and which is not a "condition where the fasting blood glucose level (glucose concentration of venous plasma) is less than 110 mg/dl or the 2-hour value (glucose concentration of venous plasma) of the 75 g oral glucose tolerance test (75 g OGTT) is less than 140 mg/dl" (normal type), is called a "borderline type".

In addition, regarding diagnostic criteria for diabetes, new diagnostic criteria were reported by ADA (The American Diabetes Association) in 1997 and by WHO in 1998.

According to these reports, diabetes is a condition where the fasting blood glucose level (glucose concentration in venous plasma) is not less than 126 mg/dl, and the 2-hour value (glucose concentration in venous plasma) of the 75 g oral glucose tolerance test is not less than 200 mg/dl.

In addition, according to the above reports, impaired glucose tolerance is a condition where the fasting blood glucose level (glucose concentration in venous plasma) is less than 126 mg/dl, and the 2-hour value (glucose concentration in venous plasma) of the 75 g oral glucose tolerance test is not less than 140 mg/dl and less than 200 mg/dl. Furthermore, according to the ADA report, a condition where the fasting blood glucose level (glucose concentration in venous plasma) is not less than 110 mg/dl and less than 126 mg/dl, is called IFG (Impaired Fasting Glucose). On the other hand, according to the WHO report, of the conditions of IFG (Impaired Fasting Glucose), a condition where the 2-hour value (glucose concentration in venous plasma) of the 75 g oral glucose tolerance test is less than 140 mg/dl, is called IFG (Impaired Fasting Glycemia).

The compound of the present invention can be used as an improving agent or an agent for the prophylaxis or treatment of diabetes, borderline type, impaired glucose tolerance, IFG (Impaired Fasting Glucose) and IFG (Impaired Fasting Glycemia) as defined by the above-mentioned new diagnostic criteria. Furthermore, the compound of the present invention can be also used as a therapeutic agent for hypertension of hypertensive patients showing a level not less than the above-mentioned diagnostic criteria (e.g., fasting blood glucose level of 126 mg/dl). Moreover, the compound of the present invention can be also used to prevent the progression of the borderline type, impaired glucose tolerance, IFG (Impaired Fasting Glucose) or IFG (Impaired Fasting Glycemia) to diabetes.

The compound of the present invention is useful as an agent for the prophylaxis or treatment of metabolic syndrome. Because patients with metabolic syndrome have an extreme high incidence of cardiovascular diseases as compared to patients with single lifestyle-related diseases, the prophylaxis or treatment of metabolic syndrome is quite important to prevent cardiovascular diseases Criteria for diagnosis of metabolic syndrome are announced by WHO in 1999, and by NCEP in 2001. According to the criterion of WHO, patients with at least two of abdominal obesity, dyslipidemia (high serum triglycerides or low HDL cholesterol), hypertension in addition to hyperinsulinemia or fasting blood glucose are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in America, patients with at least three of abdominal obesity, high triglycerides, low HDL cholesterol, hypertension and fasting blood glucose are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can be used for treating patients of high blood pressure with metabolic syndrome.

Because compound A has an anti-inflammatory action, the compound of the present invention can be used as an anti-inflammatory agent for preventing or treating inflammatory diseases. Examples of inflammatory diseases include inflammatory diseases due to various diseases such as arthritis (e.g. rheumatoid arthritis, osteoarthritis, rheumatoid myelitis, gouty arthritis, synovitis), asthma, allergic diseases, arteriosclerosis including atherosclerosis (aneurysm, coronary sclerosis, cerebral arterial sclerosis, peripheral arterial sclerosis etc.), digestive tract disease such as inflammatory intestine disease (e.g. Crohn's disease, ulcerative colitis), diabetic complication (diabetic nerves disorder, diabetic vascular disorder), atopic dermatitis, chronic obstructive pulmonary disease, systemic lupus erythematosus, visceral inflammatory disease (nephritic, hepatitis), autoimmune hemolytic anemia, psoriasis, nervous degenerative disease (e.g. Alzheimer's disease, Parkinson's diseases, amyotrophic lateral sclerosis, AIDS encephalopathy), central nervous disorder (e.g. cerebrovascular disorder such as cerebral hemorrhage and cerebral infarct, head trauma, spinal damage, cerebral edema, multiple sclerosis), meningitis, angina, cardiac infarct, congestive cardiac failure, vascular hypertrophy or occlusion and organ disorder after intervention (transdermal coronary plasty, stent indwelling, coronary endoscope, intravascular ultrasound, intracoronary thrombolysis etc), vascular reocclusion or restenosis after bypass operation, endothelial functional disorder, other circulatory disease (intermittent claudication, obstructive peripheral circulatory disorder, obstructive arteriosclerosis, obstructive thrombotic angitis, ischemic cerebral circulatory disorder, Reynaud's disease, Berger's disease), inflammatory ocular disease, inflammatory pulmonary disease (e.g. chronic pneumonia, silicosis, pulmonary sarcoidosis, pulmonary tuberculosis), endometritis, toxemia (e.g. sepsis, septic shock, endotoxin shock, gram negative sepsis, toxin shock syndrome), cachexia (e.g. cachexia due to infection, carcinomatous cachexia, cachexia due to acquired immunodeficiency syndrome), cancer, Addison's disease, Creutzfeldt-Jakob disease, virus infection (e.g. infection of virus such as cytomegalovirus, influenza virus, herpes etc.), disseminated intravascular coagulation.

In addition, because compound A has an analgesic action, the compound of the present invention can be also used as an analgesic agent for preventing or treating pain. Examples of pain diseases include acute pain due to inflammation, pain associated with chronic inflammation, pain associated with acute inflammation, pain after operation (pain of incisional, deep pain, organ pain, chronic pain after operation etc.), muscular pain (muscular pain associated with chronic pain disease, shoulder stiffness etc.), arthralgia, toothache, gnathicarthralgia, headache (migraine, catatonic headache, headache associated with fever, headache associated hypertension), organ pain (cardiac pain, angina pain, abdominal pain, renal pain, ureterane pain, bladder pain), pain in obstetrics area (mittelschmerz, dysmenorrheal, labor pain), neuralgia, (disc hernia, nerve root pain, neuralgia after herpes zoster, trigeminal neuralgia), carcinomatous pain, reflex sympathetic atrophy, complex local pain syndrome, and the like. The compound of the present invention is effective in alleviate directly and rapidly various pains such as nervous pain, carcinomatous pain and inflammatory pain, and exhibits the particularly excellent analgesic effect to patients and pathologies in which a pain sense threshold is lowered.

The compound of the present invention is particularly useful as an analgesic agent for pain associated with chronic inflammation or pain associated with hypertension, or as an agent for preventing or treating inflammatory disease or pain due to (1) arteriosclerosis including atherosclerosis, (2) vascular hypertrophy, occlusion or organ disorder after intervention, (3) reocclusion, restenosis or endothelial functional disorder after bypass operation, (4) intermittent claudication, (5) occlusive peripheral circulatory disorder, (6) occlusive arteriosclerosis.

The compound of the present invention can be used as a safe pharmaceutical agent to mammals (e.g., human, monkey, cat, swine, horse, bovine, mouse, rat, guinea pig, dog, rabbit and the like) in the form of the compound as it is or a pharmaceutical composition after admixing with a pharmacologically acceptable carrier according to a method known per se.

As used herein, as the pharmacologically acceptable carrier, various organic or inorganic carrier substances conventionally used as materials for preparations can be used. For example, excipient, lubricant, binder and disintegrant for solid preparations; solvent, dissolution aids, suspending agent, isotonizing agent and buffer for liquid preparations; and the like can be mentioned. Where necessary, additives for preparation, such as preservative, antioxidant, coloring agent, sweetening agent and the like, can be also used.

Preferable examples of excipient include lactose, sucrose, D-mannitol, D-sorbitol, starch, pregelatinized starch, dextrin, crystalline cellulose, low-substituted hydroxypropyl cellulose, carboxymethyl cellulose sodium, gum arabic, pullulan, light silicic anhydride, synthetic aluminum silicate, magnesium aluminometasilicate and the like.

Preferable examples of lubricant include magnesium stearate, calcium stearate, talc, colloidal silica and the like.

Preferable examples of binder include pregelatinized starch, sucrose, gelatin, gum arabic, methyl cellulose, carboxymethyl cellulose, carboxymethyl cellulose sodium, crystalline cellulose, sucrose, D-mannitol, trehalose, dextrin, pullulan, hydroxypropyl cellulose, hydroxypropylmethyl cellulose, polyvinylpyrrolidone and the like.

Preferable examples of disintegrant include lactose, sucrose, starch, carboxymethyl cellulose, carboxymethyl cellulose calcium, croscarmellose sodium, carboxymethyl starch sodium, light silicic anhydride, low-substituted hydroxypropyl cellulose and the like.

Preferable examples of solvent include water for injection, physiological brine, Ringer's solution, alcohol, propylene glycol, polyethylene glycol, sesame oil, corn oil, olive oil, cottonseed oil and the like.

Preferable examples of dissolution aids include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferable examples of suspending agent include surfactants such as stearyltriethanolamine, sodium lauryl sulfate, lauryl aminopropionate, lecithin, benzalkonium chloride, benzethonium chloride, glycerol monostearate etc.; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose etc.; polysorbates, polyoxyethylene hydrogenated castor oil and the like.

Preferable examples of isotonizing agent include sodium chloride, glycerin, D-mannitol, D-sorbitol, glucose and the like.

Preferable examples of buffer include buffers such as phosphate, acetate, carbonate, citrate etc., and the like.

Preferable examples of preservative include p-oxybenzoate, chlorobutanol, benzyl alcohol, phenethyl alcohol, dehydroacetic acid, sorbic acid and the like.

Preferable examples of antioxidant include sulfite, ascorbate and the like.

Preferable examples of coloring agent include water-soluble edible tar dyes (e.g., food colors such as Food Red Nos. 2 and 3, Food Yellow Nos. 4 and 5, Food Blue Nos. 1 and 2 etc.), water-insoluble Lake dyes (e.g., aluminum salts of the aforementioned water-soluble edible tar dyes etc.), natural colors (e.g., β-carotene, chlorophyll, iron oxide red etc.) and the like.

Preferable examples of sweetening agent include saccharin sodium, dipotassium glycyrrhizinate, aspartame, stevia and the like.

The dosage form of the pharmaceutical composition includes, for example, oral agents such as tablet, capsule (including soft capsule and microcapsule), granule, powder, syrup, emulsion, suspension, sustained-release preparation and the like, which can be each safely administered orally.

The pharmaceutical composition can be prepared by conventional methods in the field of pharmaceutical manufacturing technical field, such as methods described in the Japanese Pharmacopoeia, and the like. Specific production methods for such preparations are hereinafter described in detail.

For example, a tablet is produced by adding, for example, excipients (e.g., lactose, sucrose, starch, D-mannitol etc.), disintegrants (e.g., carboxymethyl cellulose calcium etc.), binders (e.g., pregelatinized starch, gum arabic, carboxymethyl cellulose, hydroxypropyl cellulose, polyvinylpyrrolidone etc.), lubricants (e.g., talc, magnesium stearate, polyethylene glycol 6000 etc.) and the like, to the active ingredient, compression-shaping, and, where necessary, applying a coating by a method known per se using coating base known per se for the purpose of achieving taste masking, enteric dissolution or sustained release.

The capsule can be made as a hard capsule filled with a powder or granular pharmaceutical agent, or a soft capsule filled with a liquid or suspension liquid. The hard capsule is produced by mixing and/or granulating an active ingredient with, for example, an excipient (e.g., lactose, sucrose, starch, crystalline cellulose, D-mannitol and the like), a disintegrant (low substituted hydroxypropyl cellulose, carmellose calcium, corn starch, croscarmellose sodium and the like), a binder (hydroxypropyl cellulose, polyvinylpyrrolidone, hydroxypropylmethyl cellulose and the like), a lubricant (magnesium stearate and the like) and the like, and filling the mixture or granule in a capsule formed from the aforementioned gelatin, hydroxypropylmethyl cellulose and the like. The soft capsule is produced by dissolving or suspending the active ingredient in a base (soybean oil, cottonseed oil, medium chain fatty acid triglyceride, beeswax and the like) and sealing the prepared solution or suspension in a gelatin sheet using, for example, a rotary filling machine and the like.

When compound (I) is a salt and avoidance of contact of compound (I) in the form of a salt with water is preferable, compound (I) is preferably dry-mixed with an excipient and the like to give a hard capsule.

The content of compound (I) in a pharmaceutical composition is generally about 0.01-about 99.9 wt %, preferably about 0.1-about 50 wt %, relative to the entire preparation.

The dose of compound (1) is determined in consideration of age, body weight, general health condition, sex, diet, administration time, administration method, clearance rate, combination of drugs, the level of disease for which the patient is under treatment then, and other factors.

While the dose varies depending on the target disease, condition, subject of administration, administration method and the like, for oral administration as a therapeutic agent for essential hypertension in adult, the daily dose of 0.1-100 mg is preferably administered in a single dose or in 2 or 3 portions.

In addition, because the compound of the present invention is superior in safety, it can be administered for a long period.

The compound of the present invention can be used in combination with pharmaceutical agents such as a therapeutic agent for diabetes, a therapeutic agent for diabetic complications, an anti-hyperlipidemia agent, an anti-arteriosclerotic agent, an anti-hypertensive agent, an anti-obesity agent, a diuretic, an antigout agent, an antithrombotic agent, an anti-inflammatory agent, a chemotherapeutic agent, an immunotherapeutic agent, a therapeutic agent for osteoporosis, an anti-dementia agent, an erectile dysfunction amelioration agent, a therapeutic agent for urinary incontinence/urinary frequency and the like (hereinafter to be abbreviated as a combination drug). On such occasions, the timing of administration of the compound of the present invention and that of the combination drug is not limited, as long as the compound of the present invention and the combination drug are combined. As the mode of such administration, for example, (1) administration of a single preparation obtained by simultaneous formulation of the compound of the present invention and a combination drug, (2) simultaneous administration of two kinds of preparations obtained by separate formulation of the compound of the present invention and a combination drug, by a single administration route, (3) time staggered administration of two kinds of preparations obtained by separate formulation of the compound of the present invention and a combination drug, by the same administration route, (4) simultaneous administration of two kinds of preparations obtained by separate formulation of the compound of the present invention and a combination drug, by different administration routes, (5) time staggered administration of two kinds of preparations obtained by separate formulation of the compound of the present invention and a combination drug, by different administration routes, such as administration in the order of the compound of the present invention and then the combination drug, or administration in a reversed order, and the like can be mentioned. The dose of the combination drug can be appropriately determined based on the dose clinically employed. The mixing ratio of the compound of the present invention and the combination drug can be appropriately selected according to the administration subject, administration route, target disease, condition, combination, and other factors. In cases where the administration subject is human, for example, the combination drug may be used in an amount of 0.01 to 100 parts by weight per part by weight of the compound of the present invention.

As the therapeutic agent for diabetes, for example, insulin preparations (e.g., animal insulin preparations extracted from the bovine or swine pancreas; human insulin preparations synthesized by a genetic engineering technique using *E. coli* or a yeast, and the like), other insulin sensitizers (e.g., pioglitazone hydrochloride, troglitazone, rosiglitazone, GI-262570, JTT-501, MCC-555, YM-440, KRP-297, CS-011, FK-614 etc.), α-glucosidase inhibitors (e.g., voglibose, acarbose, miglitol, emiglitate etc.), biguanides (e.g., phenformin, metformin, buformin etc.), insulin secretagogues [e.g., sulfonylureas (e.g., tolbutamide, glibenclamide, gliclazide, chlorpropamide, tolazamide, acetohexamide, glyclopyramide, glimepiride, glipizide, glybuzole etc.), repaglinide, senaglinide, nateglinide, mitiglinide or its calcium salt hydrate, GLP-1 etc.], amyrin agonists (e.g., pramlintide etc.), phosphotyrosine phosphatase inhibitors (e.g., vanadic acid etc.), dipeptidylpeptidase IV inhibitors (e.g., NVP-DPP-278, PT-100, P32/98 etc.), β3 agonists (e.g., CL-316243, SR-58611-A, UL-TG-307, SB-226552, AJ-9677, BMS-196085, AZ40140 etc.), gluconeogenesis inhibitors (e.g., glycogen phosphorylase inhibitor, glucose-6-phosphatase inhibitor, glucagon antagonist etc.), SGLT (sodium-glucose cotransporter) inhibitors (e.g., T-1095 etc.) and the like, can be mentioned.

As the therapeutic agents for diabetic complications, for example, aldose reductase inhibitors (e.g., tolrestat, epalrestat, zenarestat, zopolrestat, minalrestat, fidarestat, SNK-860, CT-112 etc.), neurotrophic factors (e.g., NGF, NT-3, BDNF etc.), PKC inhibitors (e.g., LY-333531 etc.), AGE inhibitors (e.g., ALT946, pimagedine, pyratoxathine, N-phenacylthiazolium bromide (ALT766), EXO-226 etc.), active oxygen scavengers (e.g., thioctic acid etc.), cerebral vasodilators (e.g., tiapride, mexiletine etc.) and the like can be mentioned.

As the anti-hyperlipidemia agents, for example, statin compounds which are cholesterol synthesis inhibitors (e.g., cerivastatin, pravastatin, simvastatin, lovastatin, atorvastatin, fluvastatin, itavastatin or salts thereof (e.g., sodium salt etc.) etc.), squalene synthetase inhibitors (e.g. TAK-475 etc.) or fibrate compounds having a triglyceride lowering effect (e.g., bezafibrate, clofibrate, simfibrate, clinofibrate etc.) and the like can be mentioned.

As the anti-arteriosclerotic agents, for example, an acyl-Coenzyme A cholesterol acyltransferase (ACAT) inhibitor (e.g. melinamide, CS-505 etc.) and a lipid rich plaque regressing agent (e.g. compounds described in WO 02/06264, WO 03/059900 etc.) and the like can be mentioned.

As the antihypertensive agents, for example, angiotensin converting enzyme inhibitors (e.g., captopril, enalapril, delapril etc.), angiotensin II antagonists (e.g., candesartan cilexetil, candesartan, losartan, losartan potassium, eprosartan, valsartan, termisartan, irbesartan, tasosartan, olmesartan, olmesartan medoxomil etc.), calcium antagonists (e.g., manidipine, nifedipine, amlodipine, efonidipine, nicardipine etc.), β-blocker (e.g., metoprolol, atenolol, propranolol, carvedilol, pindolol etc.), clonidine and the like can be mentioned.

As the anti-obesity agents, for example, central acting anti-obesity agent (e.g., dexfenfluramine, fenfluramine, phentermine, sibutramine, amfepramone, dexamphetamine, mazindol, phenylpropanolamine, clobenzorex etc.), pancreatic lipase inhibitors (e.g., orlistat etc.), β3 agonist (e.g., CL-316243, SR-58611-A, UL-TG-307, SB-226552, AJ-9677, BMS-196085, AZ40140 etc.), anorectic peptides (e.g., leptin, CNTF (ciliary neurotropic factor) etc.), cholecystokinin agonists (e.g., lintitript, FPL-15849 etc.) and the like can be mentioned.

As the diuretics, for example, xanthine derivatives (e.g., theobromine and sodium salicylate, theobromine and calcium salicylate etc.), thiazide preparations (e.g., ethiazide, cyclopenthiazide, trichlormethiazide, hydrochlorothiazide, hydroflumethiazide, benzylhydrochlorothiazide, penfluthiazide, poly 5 thiazide, methyclothiazide etc.), anti-aldosterone preparations (e.g., spironolactone, triamterene etc.), carbonic anhydrase inhibitors (e.g., acetazolamide etc.), chlorobenzenesulfonamide preparations (e.g., chlortalidone, mefruside, indapamide etc.), azosemide, isosorbide, ethacrynic acid, piretanide, bumetanide, furosemide and the like can be mentioned.

As the antigout agents, for example, allopurinol, probenecid, colchicine, benzbromarone, febuxostat, citrate and the like can be mentioned.

As the antithrombotic agents, for example, anticoagulating agent [e.g., heparin sodium, heparin potassium, warfarin potassium (warfarin), activated blood coagulation factor X inhibitor (e.g., compounds described in WO 2004/048363 etc.)], thrombolytic agent [e.g., tPA, urokinase], antiplatelet agent [e.g., aspirin, sulfinpyrazone (anturan), dipyridamole (persantin), ticlopidine (panaldine), cilostazol (pletal), GPIIb/IIIa antagonist (ReoPro), clopidogrel etc.], and the like can be mentioned.

As the antiinflammatory agents, for example, non-steroidal antiinflammatory agents, such as acetaminophen, fenasetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizol, tiaramide hydrochloride, zaltoprofen, gabexate mesilate, camostat mesilate, ulinastatin, colchicine, probenecid, sulfinpyrazone, benzbromarone, allopurinol, sodium gold thiomalate, sodium hyaluronate, sodium salicylate, morphine hydrochloride, salicylic acid, atropine, scopolamine, morphine, pethidine, levorphanol, ketoprofen, naproxen, oxymorphone and their salts etc., and the like can be mentioned.

As the chemotherapeutic agents, for example, alkylating agents (e.g., cyclophosphamide, ifosphamide etc.), metabolic antagonists (e.g., methotrexate, 5-fluorouracil etc.), anticancer antibiotics (e.g., mitomycin, adriamycin etc.), plant-derived anticancer agents (e.g., vincristine, vindesine, taxol etc.), cisplatin, carboplatin, etoposide and the like can be mentioned. Of these, furtulon, neofurtulon etc., which are 5-fluorouracil derivatives, and the like are preferable.

As the immunotherapeutic agents, for example, microorganism or bacterial components (e.g., muramyl dipeptide derivative, picibanil etc.), polysaccharides having immunostimulant activity (e.g., lentinan, schizophyllan, krestin etc.), cytokines obtained by genetic engineering techniques (e.g., interferon, interleukin (IL) etc.), colony stimulating factor (e.g., granulocyte-colony stimulating factor, erythropoietin etc.) and the like can be mentioned, with preference given to IL-1, IL-2, IL-12 and the like.

As the therapeutic agents for osteoporosis, for example, alfacalcidol, calcitriol, elcatonin, calcitonin salmon, estriol, ipriflavone, pamidronate disodium, alendronate sodium hydrate, incadronate disodium and the like can be mentioned.

As the anti-dementia agents, for example, tacrine, donepezil, rivastigmine, galantamine and the like can be mentioned.

As the erectile dysfunction amelioration agents, for example, apomorphine, sildenafil citrate and the like can be mentioned.

As the therapeutic agent for urinary incontinence/urinary frequency, for example, flavoxate hydrochloride, oxybutynin hydrochloride, propiverine hydrochloride and the like can be mentioned.

Moreover, pharmaceutical agents having a cachexia improving effect acknowledged in animal models and clinical situations, which include cyclooxygenase inhibitors (e.g., indomethacin etc.)[*Cancer Research*, Vol. 49, 5935-5939 pages, 1989], progesterone derivatives (e.g., megestrol acetate) [*Journal of Clinical Oncology*, Vol. 12, 213-225 pages, 1994], glucosteroid (e.g., dexamethasone etc.), metoclopramide pharmaceutical agents, tetrahydrocannabinol pharmaceutical agent (publications are the same as the above), fat metabolism improving agent (e.g., eicosapentanoic acid etc.)[*British Journal of Cancer*, Vol. 68, pp. 314-318, 1993], growth hormone, IGF-1, and antibodies against TNF-α, LIF, IL-6 and oncostatin M, which induce cachexia, and the like, can be also used in combination with the pharmaceutical agent of the present invention.

The combination drug preferably includes a diuretic, an insulin preparation, an insulin sensitizer, an α-glucosidase inhibitor, a biguanide agent, an insulin secretagogue (preferably sulfonylurea agent) and the like. Particularly, a diuretic such as hydrochlorothiazide and the like and an insulin sensitizers such as pioglitazone hydrochloride and the like are preferable.

The above-mentioned combination drug may be a combination of two or more kinds thereof combined at appropriate ratios.

Since the compound of the present invention potentiates hypoglycemic activity of other insulin sensitizers, a combined use of the compound of the present invention and other insulin sensitizers (preferably pioglitazone hydrochloride) markedly enhances a prophylactic and/or therapeutic effect against diseases in which insulin resistance is involved, such as type II diabetes and the like.

The compound of the present invention shows a superior prophylactic or therapeutic effect against circulatory diseases such as hypertension and the like and metabolic diseases such as diabetes and the like.

EXAMPLES

The present invention is explained in detail by referring to the following Examples, Preparation Examples and Experimental Examples. However, these Examples are mere practical embodiments and do not limit the present invention. The present invention may be modified as long as the scope of the invention is not deviated.

The elution by column chromatography in Examples was performed under observation by TLC (thin-layer chromatography). In the TLC observation, 60F$_{254}$ (Merck) was used as a TLC plate, the solvent used as an elution solvent in the column chromatography was used as a developing solvent, and UV detector was used for detection. As silica gel for column, Kieselgel 60 (70-230 mesh) or Kieselgel 60 (230-400 mesh) manufactured by Merck was used. NMR spectrum was measured using tetramethylsilane as an internal or external standard, and the chemical shift is expressed in δ value and the coupling constant is expressed in Hz. The symbols in the Examples mean the following.

s: singlet
d: doublet
t: triplet
q: quartet
dd: double doublet
m: multiplet
J: coupling constant
THF: tetrahydrofuran
DMF: dimethylformamide
DMSO: dimethyl sulfoxide
DBU: 1,8-diazabicyclo[5.4.0]-7-undecene

Example 1

(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate To a solution of disodium 2-ethoxy-1-{[2'-(5-oxo-4,5-dihydro-1,2,4-oxadiazol-3-yl)biphenyl-4-yl]methyl}-1H-benzimidazole-7-carboxylate (2.0 g) in DMF (20 mL) was added 4-chloromethyl-5-methyl-1,3-dioxol-2-one (0.99 g) and the mixture was stirred at room temperature for 12 hrs. The reaction mixture was concentrated and the residue was dissolved in chloroform and 1N hydrochloric acid. The organic layer was separated, dried over anhydrous sodium sulfate and concentrated. The residue was purified by silica gel column chromatography to give the title compound (0.26 g, 14%) as a colorless solid.

$^1$H NMR (300 MHz, CDCl$_3$) δ: 1.43 (3H, t, J=7.1 Hz), 2.14 (3H, s), 4.46 (2H, q, J=7.1 Hz), 4.87 (2H, s), 5.63 (2H, s), 6.93 (2H, d, J=8.3 Hz), 7.07 (1H, t, J=7.9 Hz), 7.16 (2H, d, J=8.1 Hz), 7.32-7.37 (2H, m), 7.53-7.64 (3H, m), 7.83 (1H, dd, J=1.4 Hz, 7.6 Hz)

Example 2

(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate To a solution of 2-ethoxy-1-{[2'-(5-oxo-4,5-dihydro-1,2,4-oxadiazol-3-yl)biphenyl-4-yl]methyl}-1H-benzimidazole-7-carboxylic acid (5.0 g) and triethylamine (1.69 mL) in THF (50 mL) was added dropwise 2,4,6-trichlorobenzoyl chloride (1.81 mL) under ice-cooling. After stirring the mixture at room temperature for 12 hrs, insoluble material was filtered off and the filtrate was concentrated. The residue was dissolved in methylene chloride (50 mL), and 4-hydroxymethyl-5-methyl-1,3-dioxol-2-one (1.72 g) and N,N-dimethylaminopyridine (1.61 g) were added under ice-cooling. After stirring the mixture at room temperature for 4 hrs, the reaction mixture was diluted with chloroform (150 mL), washed with water, saturated aqueous sodium hydrogen carbonate, 1N hydrochloric acid and saturated brine, dried over anhydrous sodium sulfate and concentrated. The residue was crystallized from diisopropyl ether to give crude crystals. The crude crystals were dissolved in ethanol (18 mL) with refluxing. Activated carbon (0.1 g) was added to the solution and the mixture was stirred with refluxing for 30 min. Insoluble material was filtered off and the filtrate was allowed to cool to room temperature. After 12 hrs., the precipitated crystals were collected by filtration and the crystals were washed with ice-cooled ethanol and dried under reduced pressure at room temperature to give the title compound (3.0 g, 50%). 4-Hydroxymethyl-5-methyl-1,3-dioxol-2-one was synthesized by the method described in Alpegiani, M.; Zarini, F.; Perrone, E. Synthetic Communication, Vol. 22, pp. 1277-1282 (1992).

$^1$H NMR (300 MHz, DMSO-d$_6$) δ: 1.37 (3H, t, J=7.2 Hz), 2.14 (3H, s), 4.58 (2H, q, J=7.2 Hz), 5.10 (2H, s), 5.53 (2H, s), 6.97 (2H, d, J=7.8 Hz), 7.17-7.22 (3H, m), 7.44-7.53 (3H, m), 7.61-7.73 (3H, m).

Example 3

2-oxo-1,3-dioxolan-4-yl 2-ethoxy-1-{[2'-(5-oxo-4,5-dihydro-1,2,4-oxadiazol-3-yl)biphenyl-4-yl]methyl}-1H-benzimidazole-7-carboxylate A solution of 2-ethoxy-1-{[2'-(5-oxo-4,5-dihydro-1,2,4-oxadiazol-3-yl)biphenyl-4-yl]methyl}-1H-benzimidazole-7-carboxylic acid (1.0 g), 4-chloro-1,3-dioxolan-2-one (0.41 g) and triethylamine in DMF was stirred at 90° C. for 12 hrs. The reaction mixture was concentrated, and the residue was dissolved in chloroform and 1N hydrochloric acid. The organic layer was separated, dried over anhydrous sodium sulfate and concentrated. The residue was purified by silica gel column chromatography to give the title compound (0.20 g, 22%) as a colorless solid.

$^1$H NMR (300 MHz, DMSO-D$_6$) δ: 1.39 (3H, t, J=7.1 Hz), 4.52-4.65 (3H, m), 4.78 (1H, dd, J=5.8 Hz, 10.1 Hz), 5.55 (2H, d, J=2.6 Hz), 6.84 (1H, dd, J=2.1 Hz, 5.6 Hz), 7.03 (2H, d, J=8.3 Hz), 7.20-7.25 (3H, m), 7.43-7.57 (2H, m), 7.60-7.69 (3H, m), 7.77 (1H, dd, J=1.0 Hz, 7.8 Hz).

Example 4

4-methyl-2-oxo-1,3-dioxolan-4-yl 2-ethoxy-1-{[2'-(5-oxo-4,5-dihydro-1,2,4-oxadiazol-3-yl)biphenyl-4-yl]methyl}-1H-benzimidazole-7-carboxylate The title compound (0.21 g, 11%) was obtained from 2-ethoxy-1-{[2'-(5-oxo-4,5-dihydro-1,2,4-oxadiazol-3-yl)biphenyl-4-yl]methyl}-1H-benzimidazole-7-carboxylic acid (2.0 g) and 4-chloro-4-methyl-1,3-dioxolan-2-one (1.2 g) according to a method similar to the method of Example 3. 4-Chloro-4-methyl-1,3-dioxolan-2-one was synthesized according to the method described in JP-A-62-290071.

$^1$H NMR (300 MHz, CDCl$_3$) δ: 1.41 (3H, t, J=7.1 Hz), 1.81 (3H, s), 4.53 (2H, d, J=3.6 Hz), 4.63 (2H, q, J=7.1 Hz), 5.57 (2H, d, J=6.4 Hz), 6.96 (2H, d, J=8.1 Hz), 7.20-7.28 (3H, m), 7.46 (1H, d, J=7.9 Hz), 7.54-7.69 (4H, m), 7.78 (1H, d, J=7.9 Hz).

Example 5

(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt The compound (0.55 g) obtained in Example 1 or 2 was dissolved in acetone (10 mL) at 50° C. The solution was ice-cooled and a solution of potassium 2-ethylhexanoate (0.17 g) in acetone (2 mL) was added dropwise. The mixture was left standing overnight in a refrigerator, and the precipitated crystals were collected by filtration and dried under reduced pressure at room temperature to give the title compound (0.37 g, 63%). melting point: 196° C. (dec.)

$^1$H NMR (300 MHz, DMSO-d$_6$) δ: 1.42 (3H, t, J=7.1 Hz), 2.17 (3H, s), 4.62 (2H, q, J=7.1 Hz), 5.11 (2H, s), 5.51 (2H, s), 6.85 (2H, d, J=8.3 Hz), 7.16-7.27 (4H, m), 7.30-7.42 (2H, m), 7.44-7.52 (2H, m), 7.72 (1H, dd, J=1.1 Hz, 7.9 Hz).

Example 6

(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate sodium salt The compound (10 g) obtained in Example 1 or 2 was dissolved in THF (200 mL) at 50° C. The solution was ice-cooled and a solution of sodium 2-ethylhexanoate (2.93 g) in THF (2 mL) was added dropwise. The reaction mixture was concentrated and the residue was washed with diethyl ether and the crystals were collected by filtration. The crystals were dried under reduced pressure at 50° C. to give the title compound (8.52 g, 82%) as a colorless solid.

$^1$H NMR (300 MHz, DMSO-D$_6$) δ: 1.41 (3H, t, J=7.1 Hz), 2.16 (3H, s), 4.61 (2H, q, J=7.1 Hz), 5.11 (2H, s), 5.53 (2H, s), 6.91 (2H, d, J=8.4 Hz), 7.19-7.28 (4H, m), 7.29-7.68 (4H, m), 7.76 (1H, m).

Example 7

(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate calcium salt adduct with calcium acetate The compound (1.0 g) obtained in Example 6 was dissolved in acetonitrile (10 mL) at room temperature. A solution of calcium acetate monohydrate (0.26 g) in acetonitrile (10 mL) was added dropwise to the solution at room temperature. The reaction mixture was stirred overnight and the precipitated crystals were collected by filtration. The crystals were dried under reduced pressure at 50° C. to give the title compound (0.78 g, 56%) as a colorless solid.

$^1$H NMR (300 MHz, DMSO-D$_6$) δ: 1.42 (3H, t, J=7.2 Hz), 1.78 (9H, s), 2.17 (3H, s), 4.62 (2H, q, J=7.2 Hz), 5.11 (1H, s), 5.51 (1H, s), 6.84 (2H, d, J=7.4 Hz), 7.18-7.23 (4H, m), 7.28-7.40 (2H, m), 7.47-7.50 (2H, m), 7.69-7.74 (1H, m).

Example 8

5-oxotetrahydro-2-furanyl 2-ethoxy-1-{[2'-(5-oxo-4,5-dihydro-1,2,4-oxadiazol-3-yl)biphenyl-4-yl]methyl}-1H-benzimidazole-7-carboxylate To a solution of 2-ethoxy-1-{[2'-(5-oxo-4,5-dihydro-1,2,4-oxadiazol-3-yl)biphenyl-4-yl]methyl}-1H-benzimidazole-7-carboxylic acid (4.0 g) and triethylamine (1.3 mL) in THF (50 mL) was added dropwise 2,4,6-trichlorobenzoyl chloride (1.4 mL) under ice-cooling. After stirring at room temperature for 12 hrs., insoluble material was filtered off and the filtrate was concentrated. The residue was dissolved in methylene chloride (50 mL) and 5-oxotetrahydro-2-furanyl (0.67 g) and N,N-dimethylaminopyridine (1.0 g) were added under ice-cooling. After stirring at room temperature for 4 hrs., the reaction mixture was diluted with chloroform (150 mL), washed with water, saturated aqueous sodium hydrogen carbonate, 1 N hydrochloric acid and saturated brine, dried over anhydrous sodium sulfate and concentrated. The residue was purified by silica gel column chromatography to give the title compound (0.16 g, 3.3%) as a colorless solid.

$^1$H NMR (300 MHz, CDCl$_3$) δ: 1.48 (3H, t, J=7.1 Hz), 2.31-2.39 (1H, m), 2.45-2.66 (2H, m), 2.67-2.79 (1H, m), 4.63 (2H, q, J=7.1 Hz), 5.61 (1H, d, J=18 Hz), 5.81 (1H, d, J=18 Hz), 6.71-6.73 (1H, m), 6.98-7.01 (2H, m), 7.16-7.25 (3H, m), 7.36-7.38 (1H, m), 7.48-7.59 (3H, m), 7.69-7.80 (2H, m)

Example 9

(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate To a solution of 2-ethoxy-1-{[2'-(5-oxo-4,5-dihydro-1,2,4-oxadiazol-3-yl)biphenyl-4-yl]methyl}-1H-benzimidazole-7-carboxylic acid (9.0 g) and 4-hydroxymethyl-5-methyl-1,3-dioxol-2-one (3.08 g) in N,N-dimethylacetamide (100 mL) were added p-toluenesulfonyl chloride (4.13 g), N,N-dimethylaminopyridine (0.48 g) and potassium carbonate (3.54 g) under ice-cooling and the mixture was stirred at about 10° C. for 3 hrs. After adjusting the pH of the mixture to about 5, the mixture was crystallized by adding water (72 mL) to give crystals as a solvate. The isolated crystals were suspended in a mixture of water (63 mL) and acetone (27 mL) and the suspension was stirred at about 35° C. for 2 hrs. After stirring under ice-cooling for 2 hrs, the crystals were collected by filtration and the crystals were washed with water (18 mL) and dried under reduced pressure at 40° C. to give the title compound (10.6 g, 95%).

$^1$H NMR (300 MHz, DMSO-d$_6$) δ: 1.39 (3H, t, J=6.4 Hz), 2.17 (3H, s), 4.60 (2H, q, J=6.4 Hz), 5.12 (2H, s), 5.56 (2H, s), 7.00 (2H, d, J=7.0 Hz), 7.22-7.24 (3H, m), 7.46-7.57 (3H, m), 7.64-7.75 (3H, m).

Formulation Examples

When the compound of the present invention is used as a therapeutic agent for circulatory diseases such as hypertension, cardiac disease, stroke, nephritis and the like, for example, the following formulation can be used.

In the following formulation, as the components (additive) other than the active ingredient, those listed in the Japanese Pharmacopoeia, the Japanese Pharmacopoeia quasi drugs or the pharmaceutical product additive standard, and the like can be used.

1. Tablet

| (1) Compound obtained in Example 1 | 10 mg |
|---|---|
| (2) Lactose | 35 mg |
| (3) Corn starch | 150 mg |
| (4) Microcrystalline cellulose | 30 mg |
| (5) Magnesium stearate | 5 mg |
| 1 tablet | 230 mg |

(1), (2), (3) and ⅔ of (4) are admixed and granulated. Thereto are added the remaining (4) and (5), and the mixture is compression formed to give tablets.

2. Capsule

| (1) Compound obtained in Example 5 | 10 mg |
|---|---|
| (2) Lactose | 69.5 mg |
| (3) Light silicic anhydride | 0.2 mg |
| (4) Magnesium stearate | 0.3 mg |
| 1 capsule | 80 mg |

(1), (2), (3) and (4) were dry mixed and filled in HPMC capsule (No. 3).

3. Tablet

| (1) Compound obtained in Example 1 | 10 mg |
|---|---|
| (2) Amlodipine besilate | 5 mg |
| (3) Lactose | 30 mg |
| (4) Corn starch | 150 mg |
| (5) Microcrystalline cellulose | 30 mg |
| (6) Magnesium stearate | 5 mg |
| 1 tablet | 230 mg |

(1), (2), (3), (4) and ⅔ of (5) are admixed and granulated. Thereto are added the remaining (5) and (6), and the mixture is compression formed to give tablets.

4. Capsule

| (1) Compound obtained in Example 5 | 10 mg |
|---|---|
| (2) Amlodipine besilate | 5 mg |
| (3) Lactose | 64.5 mg |
| (4) Light silicic anhydride | 0.2 mg |
| (5) Magnesium stearate | 0.3 mg |
| 1 capsule | 80 mg |

(1), (2), (3), (4) and (5) were dry mixed and filled in HPMC capsule (No. 3).

5. Tablet

| (1) Compound obtained in Example 1 | 10 mg |
|---|---|
| (2) Hydrochlorothiazide | 12.5 mg |
| (3) Lactose | 22.5 mg |
| (4) Corn starch | 150 mg |
| (5) Microcrystalline cellulose | 30 mg |
| (6) Magnesium stearate | 5 mg |
| 1 tablet | 230 mg |

(1), (2), (3), (4) and ⅔ of (5) are admixed and granulated. Thereto are added the remaining (5) and (6), and the mixture is compression formed to give tablets.

6. Capsule

| (1) Compound obtained in Example 5 | 10 mg |
|---|---|
| (2) Hydrochlorothiazide | 12.5 mg |
| (3) Lactose | 57 mg |
| (4) Light silicic anhydride | 0.2 mg |
| (5) Magnesium stearate | 0.3 mg |
| 1 capsule | 80 mg |

(1), (2), (3), (4) and (5) were dry mixed and filled in HPMC capsule (No. 3).

Experimental Example 1

Inhibitory Effects of Compounds of the Present Invention Against Angiotensin II Induced Pressor Response in Rats Male Sprague-Dawley rats (9-11 weeks old, CLEA Japan, Inc.) were anesthetized with pentobarbital (50 mg/kg, i.p.) and the femoral artery and vein were isolated and cannulated with polyethylene tubes filled with saline containing heparin (200 U/mL). The catheters were subcutaneously inserted to a site in the back of the neck and fixed. After recovery period, the rat was subjected to the experiment. The arterial catheter was connected to a pressure transducer coupled to a blood pressure monitor amplifier (2238, NEC San-ei Instruments) and the pressure was recorded on a recorder (RECTI-HORIZ 8K, NEC San-ei Instruments). After establishing angiotensin II (AII, 100 ng/kg, i.v.) induced pressor responses, a test compound at a dose corresponding to an equimolar amount of compound A (2-ethoxy-1-{[2'-(5-oxo-4,5-dihydro-1,2,4-oxadiazol-3-yl)biphenyl-4-yl]methyl}-1H-benzimidazole-7-carboxylic acid) was administered. AII was administered 24 hours later and increase in the blood pressure was measured, based on which the inhibition rate from the value before the administration was calculated. All compounds were suspended in 0.5% methylcellulose and orally administered at a volume of 2 mL/kg.

The results are shown in mean±SEM (Table 1). The significance between the group administered with the compound obtained in Example 5 and the other groups was analyzed using Student's t-test (**: $p > 0.01$, *: $p > 0.05$).

TABLE 1

| | 24 hrs after administration |
|---|---|
| Example 5 [0.13 mg/kg, p.o. (n = 5)] | 32.7 ± 4.6 |
| compound B [0.10 mg/kg, p.o. (n = 3)] | 0.8 ± 4.9** |
| compound C [0.14 mg/kg, p.o. (n = 5)] | 9.3 ± 8.6* |
| compound D [0.12 mg/kg, p.o. (n = 4)] | 10.9 ± 5.6* | compound B: methyl 2-ethoxy-1-{[2'-(5-oxo-4,5-dihydro-1,2,4-oxadiazol-3-yl)biphenyl-4-yl]methyl}-1H-benzimidazole-7-carboxylate
compound C: 1-(cyclohexyloxycarbonyloxy)ethyl 2-ethoxy-1-{[2'-(5-oxo-4,5-dihydro-1,2,4-oxadiazol-3-yl)biphenyl-4-yl]methyl}-1H-benzimidazole-7-carboxylate
compound D: acetoxymethyl 2-ethoxy-1-{[2'-(5-oxo-4,5-dihydro-1,2,4-oxadiazol-3-yl)biphenyl-4-yl]methyl}-1H-benzimidazole-7-carboxylate As is clear from the results, the compound of the present invention shows a significantly long lasting and potent pharmacological action by oral administration, as compared with esters described in JP-A-5-271228.

Experimental Example 2

Inhibitory Effects of the Compounds of the Present Invention Against Angiotensin II Induced Pressor Response in Dogs For the experiment, male beagles (body weight 12.0-14.7 kg, KITAYAMA LABES, CO., LTD.) were used. They were anesthetized with sodium pentobarbital (50 mg/kg, i.p.), and a tracheal tube was inserted for management of the airway. The femoral region and the back of the neck were shaved, and a disinfectant (Isodine solution, MEIJI SEIKA KAISHA, LTD.) was applied. The dog was fixed at the dorsal position and the right femoral region was incised. A mirror catheter (5F, MILLER INDUSTRIES) was inserted and placed in the femoral artery and a polyurethane tube in the femoral vein. The catheter and tube were passed through subcutaneously and fixed at the back region. The incised region was sutured thereafter and penicillin G potassium (MEIJI SEIKA KAISHA, LTD., 40000 units) was intramuscularly administered to prevent infection. Beginning from the next day, penicillin G potassium (40000 units) was administered once a day for 3 days. After 3 days for recovery, the dog was subjected to the experiment.

During the experiment, the dog was placed in a small metabolic cage. For measurement, the mirror catheter inserted in the femoral artery was connected to a transducer unit (MILLER INDUSTRIES), and the systemic blood pressure (average blood pressure) was recorded on a recorder (RECTI-HORIZ 8K, NEC San-ei Instruments) through a DC amplifier (N4777, NEC San-ei Instruments) and a blood pressure monitor amplifier (N4441, NEC San-ei Instruments). The polyurethane tube inserted in the femoral vein was fixed outside the cage and used for administration of AII (PEPTIDE INSTITUTE, INC.). The experiment was conducted under fasting and AII (100 ng/kg, i.v.) was administered 3 or 4 times before administration of a test compound to confirm stabilization of the vasopressor response. A dose of the test compound corresponding to an equimolar amount of compound A was suspended in 0.5% methylcellulose and orally administered at a volume of 2 mL/kg. After drug administration, AII was administered at each time point of measurement and increase in the blood pressure was measured, based on which the inhibition rate from the value before the administration was calculated.

The results are shown in mean±SEM (Table 2). The significance between the group administered with the compound obtained in Example 5 and the group administered with compound A was analyzed using Student's t-test with Bonferroni correction (**: $p > 0.01$, *: $p > 0.05$).

TABLE 2

| | 10 hrs after administration | 24 hrs after administration |
|---|---|---|
| compound A [1 mg/kg, p.o. (n = 6)] | 27.0 ± 3.2 | 19.6 ± 3.7 |
| Example 2 [1.25 mg/kg, p.o. (n = 6)] | 35.9 ± 4.8 | 28.6 ± 4.7 |
| Example 5 [1.33 mg/kg, p.o. (n = 5)] | 55.6 ± 3.4** | 40.3 ± 5.1* |

As is clear from the results, the compound of the present invention shows a long lasting and potent pharmacological action by oral administration.

INDUSTRIAL APPLICABILITY

The compound of the present invention is useful as an agent for the prophylaxis or treatment of circulatory diseases such as hypertension and the like and metabolic diseases such as diabetes and the like.

This application is based on a patent application No. 2004-048928 filed in Japan and U.S. patent application Ser. No. 11/031,057, the contents of which are hereby incorporated by reference.

The invention claimed is:

1. A method for improving insulin resistance in a mammal, which comprises administering an effective amount of (5-methyl-2-oxo-1,3-dioxol-4-yl)methyl 2-ethoxy-1-{[T-(5-oxo-4,5-dihydro-1,2,4-oxadiazol-3-yl)biphenyl-4-yl]methyl}-1H-benzimidazole-7-carboxylate, or a pharmaceutically acceptable salt thereof to said mammal in need thereof.

2. A method for treating of diseases in which insulin resistance is involved in a mammal, which comprises administering an effective amount of (5-methyl-2-oxo-1,3-dioxol-4-yl) methyl 2-ethoxy-1-{[2'-(5-oxo-4,5-dihydro-1,2,4-oxadiazol-3-yl)biphenyl-4-yl]methyl}-1H-benzimidazole-7-carboxylate, or a pharmaceutically acceptable salt thereof to said mammal in need thereof.

3. A method for treating of diseases in which insulin resistance is involved in a mammal, which comprises administering an effective amount of (5-methyl-2-oxo-1,3-dioxol-4-yl) methyl 2-ethoxy-1-{[2'-(5-oxo-4,5-dihydro-1,2,4-oxadiazol-3-yl)biphenyl-4-yl]methyl}-1H-benzimidazole-7-carboxylate, or a pharmaceutically acceptable salt thereof in combination with a calcium antagonist to said mammal in need thereof.

4. A method for treating of diseases in which insulin resistance is involved in a mammal, which comprises administering an effective amount of (5-methyl-2-oxo-1,3-dioxol-4-yl) methyl 2-ethoxy-1-{[2'-(5-oxo-4,5-dihydro-1,2,4-oxadiazol-3-yl)biphenyl-4-yl]methyl}-1H-benzimidazole-7-carboxylate, or a pharmaceutically acceptable salt thereof in combination with an insulin sensitizer to said mammal in need thereof.

5. A method for treating of diseases in which insulin resistance is involved in a mammal, which comprises administering an effective amount of (5-methyl-2-oxo-1,3-dioxol-4-yl) methyl 2-ethoxy-1-{[2'-(5-oxo-4,5-dihydro-1,2,4-oxadiazol-3-yl)biphenyl-4-yl]methyl}-1H-benzimidazole-7-carboxylate, or a pharmaceutically acceptable salt thereof in combination with a biguanide to said mammal in need thereof.

* * * * *